US012655055B2

(12) United States Patent
Vogl et al.

(10) Patent No.: US 12,655,055 B2
(45) Date of Patent: Jun. 16, 2026

(54) GLASS, METHOD FOR PRODUCING A GLASS, AND GLASS MELTING APPARATUS

(71) Applicant: SCHOTT AG, Mainz (DE)

(72) Inventors: Armin Vogl, Jena (DE); Joerg Hessenkemper, Jena (DE); Knut Jakobi, Jena (DE); Klaus-Dieter Duch, Taunusstein (DE); Andreas Sprenger, Rothenstein (DE); Michael Hahn, Hohenstein (DE); Klaus-Peter Koenig, Jena (DE); Thomas Pfeiffer, Ingelheim (DE)

(73) Assignee: SCHOTT AG, Mainz (DE)

( * ) Notice: Subject to any disclaimer, the term of this patent is extended or adjusted under 35 U.S.C. 154(b) by 614 days.

(21) Appl. No.: 17/749,478

(22) Filed: May 20, 2022

(65) Prior Publication Data

US 2022/0281766 A1     Sep. 8, 2022

Related U.S. Application Data

(63) Continuation of application No. PCT/EP2020/082860, filed on Nov. 20, 2020.

(30) Foreign Application Priority Data

Nov. 21, 2019     (DE) ..................... 10 2019 217 977.0

(51) Int. Cl.
| | |
|---|---|
| *C03C 3/089* | (2006.01) |
| *C03B 5/03* | (2006.01) |
| *C03B 5/167* | (2006.01) |
| *C03B 5/225* | (2006.01) |
| *C03C 3/078* | (2006.01) |
| *C03C 3/083* | (2006.01) |
| *C03C 3/087* | (2006.01) |
| *C03C 3/091* | (2006.01) |
| *C03C 3/093* | (2006.01) |
| *C03B 5/027* | (2006.01) |
| *G01N 21/59* | (2006.01) |
| *G01N 33/38* | (2006.01) |

(52) U.S. Cl.
CPC ............... *C03C 3/089* (2013.01); *C03B 5/03* (2013.01); *C03B 5/1672* (2013.01); *C03B 5/225* (2013.01); *C03C 3/078* (2013.01); *C03C 3/083* (2013.01); *C03C 3/087* (2013.01); *C03C 3/091* (2013.01); *C03C 3/093* (2013.01); *C03B 5/027* (2013.01); *C03C 2201/10* (2013.01); *C03C 2201/32* (2013.01); *C03C 2201/50* (2013.01); *C03C 2201/54* (2013.01); *C03C 2203/10* (2013.01); *G01N 21/59* (2013.01); *G01N 33/386* (2013.01)

(58) Field of Classification Search
CPC ............ C03C 3/089; C03C 3/091; C03B 5/03
See application file for complete search history.

(56) References Cited

U.S. PATENT DOCUMENTS

| | | | | |
|---|---|---|---|---|
| 6,465,381 | B1 | 10/2002 | Lautenschlaeger | |
| 6,829,908 | B2 | 12/2004 | Bowden | |
| 2003/0159465 | A1 | 8/2003 | Bowden | |
| 2006/0137402 | A1 | 6/2006 | Eichholz | |
| 2006/0144089 | A1 | 7/2006 | Eichholz | |
| 2008/0090717 | A1 | 4/2008 | Nagashima | |
| 2008/0269039 | A1* | 10/2008 | Joubaud .................... | C03C 1/02 501/66 |
| 2009/0090135 | A1 | 4/2009 | Tran | |
| 2011/0045961 | A1* | 2/2011 | Dejneka ................. | C03C 3/087 501/53 |
| 2012/0159992 | A1 | 6/2012 | Sakamoto | |
| 2013/0217561 | A1* | 8/2013 | Yang ....................... | C03C 3/093 501/67 |
| 2013/0225389 | A1* | 8/2013 | Dick ....................... | C03C 3/091 501/66 |
| 2013/0267402 | A1* | 10/2013 | Nishizawa .............. | C03C 3/087 65/99.2 |
| 2014/0230491 | A1* | 8/2014 | Bookbinder .......... | C03B 5/1675 65/29.17 |
| 2016/0145147 | A1 | 5/2016 | Annamalai | |
| 2016/0236965 | A1 | 8/2016 | Annamalai | |
| 2017/0305775 | A1 | 10/2017 | Duch | |
| 2019/0308899 | A1 | 10/2019 | Schmitt | |
| 2020/0140314 | A1 | 5/2020 | Tomamoto | |
| 2021/0039982 | A1 | 2/2021 | Schmiady | |

FOREIGN PATENT DOCUMENTS

| | | |
|---|---|---|
| CN | 101341102 | 1/2009 |
| CN | 105377776 | 3/2016 |
| DE | 10393837 | 9/2007 |
| DE | 102010037437 | 3/2012 |
| DE | 102019121146 | 2/2021 |
| EP | 1070681 | 1/2001 |
| EP | 2789587 | 10/2014 |
| EP | 3239110 | 11/2017 |

(Continued)

OTHER PUBLICATIONS

English translation of the Written Opinion of the International Searching Authority dated Feb. 23, 2021 for PCT/EP2020/082860, with English translation, 6 pages.
English translation of the International Preliminary Report dated May 17, 2022 for PCT/EP2020/082860, with English translation, 7 pages.

(Continued)

*Primary Examiner* — Elizabeth A. Bolden

(74) *Attorney, Agent, or Firm* — Ruggiero McAllister & McMahon LLC

(57) ABSTRACT

A glass element has, per kg of glass, 50 or fewer inclusions having a size of 2 μm to 10 μm. The glass element can be made of borosilicate glass.

16 Claims, 2 Drawing Sheets

(56)          References Cited

FOREIGN PATENT DOCUMENTS

| EP | 3553034      | 10/2019 |
|----|--------------|---------|
| JP | 2014501682   | 1/2014  |
| JP | 2017536323 A | 12/2017 |
| JP | 2018508453 A | 3/2018  |
| JP | 2018104265   | 7/2018  |

OTHER PUBLICATIONS

International Search Report dated Feb. 23, 2021 for PCT/EP2020/082860, with English translation, 5 pages.
Din En 410, "Glass in building—Determination of the luminous and solar characteristics of glazing", Apr. 2011, 66 pages.

* cited by examiner

GLASS, METHOD FOR PRODUCING A GLASS, AND GLASS MELTING APPARATUS

CROSS-REFERENCES TO RELATED APPLICATIONS

This application is a continuation of International Application No. PCT/EP2020/082860, filed Nov. 20, 2020, that claims priority to German Patent Application DE102019217977.0, filed Nov. 21, 2019, the entire contents of each of which are incorporated by reference.

BACKGROUND OF THE DISCLOSURE

1. Field of the Disclosure

The disclosure relates to a glass element, preferably a glass element made of borosilicate glass.

The disclosure further relates to a method for producing a glass element, preferably a glass element made of borosilicate glass.

Beyond this, the disclosure relates to a glass melting apparatus, to a method for operating a glass melting apparatus, as well as to a glass element, preferably a glass element made of borosilicate glass, preferably in the form of a borosilicate glass plate, produced by a method and/or by a glass melting apparatus.

Although, in general, the present disclosure is applicable to any glass element, the present disclosure is explained in regard to a glass element in the form of a glass plate.

2. Description of Related Art

Glass melting apparatuses for the production of glass are usually composed of a melting or heating region, in which a liquid glass melt is formed from the raw materials, the so-called glass batch; a following refining region, in which the glass melt is refined, so that the residual gas bubbles still remaining after the melting or heating process are removed from the glass melt, and from a downstream conditioning region, which serves for further conditioning of the refined glass melt. Here, the temperatures required for the overall melting process are strongly dependent on the type of glass. Thus, soda-lime glasses for the production of window glass and glass containers, for example, are melted at markedly lower temperatures than, for example, special glasses for display applications or also glass ceramics. In this case, the conditioning region of a glass melting apparatus of this kind can be designed as a working tank or also as a channel and distributor system. Usually used as wall material of a glass melting apparatus is a refractory material, generally comprising of aluminum zirconium silicate material. However, it is known that the use of materials of this kind as wall material or melt contact material can lead to the formation of bubbles and/or schlieren (streaks) in the glass melt and ultimately to rejects in the glass end product.

Moreover, other defects, such as, for example, particles or the like released from the wall material of the melting tank, lead to corresponding inclusions in the micrometer range in floated borosilicate glass, for example, thereby then making this glass unsuitable for various applications. Samples of glass plates made of floated borosilicate glass that have been produced in the known way have interfering metallic and non-metallic inclusions and bubbles having a broad size distribution and in great number. Inclusions with a size of more than 50 µm can be sorted out by means of conventional optical detection methods. By contrast, inclusions with a size of 50 µm or less can be detected only with great difficulty and in general can be identified, quantified, and qualitatively evaluated only with great effort by trained persons.

Accordingly, it has been determined by the present disclosure that there is a continuing need for a glass, method for producing glass, and glass melting apparatus that overcomes, alleviates, and/or mitigates one or more of the aforementioned and other deleterious effects of prior glasses, methods, and apparatuses.

SUMMARY

An object of the present disclosure is therefore to provide a glass element, preferably a glass plate, with a reduced number of inclusions in the micrometer range and a method for producing the glass element, preferably a glass plate, to provide a glass melting apparatus, and to present a method for operating the glass melting apparatus that substantially reduces the number of inclusions in the micrometer range.

A further object of the present disclosure is to present an alternative glass element, preferably a glass plate, an alternative method for producing a glass element, preferably a glass plate, an alternative glass melting apparatus, and an alternative method for operating the glass melting apparatus.

The present disclosure achieves the aforementioned objects by a glass element, preferably a glass element made of borosilicate glass, wherein, per kg of glass, the glass element has 50 inclusions or fewer having a size of 2 µm or more and 10 µm or less.

The present disclosure achieves the aforementioned objects by a method for producing a glass element, preferably a glass element made of borosilicate glass, comprising the steps:

i) providing a batch, comprising, in wt %:
   $SiO_2$ 60 to 90%, preferably 76% to 90%;
   $B_2O_3$ 0 to 20%;
   $Al_2O_3$ 0 to 20%;
   $Li_2O$ 0 to 10%;
   $Na_2O$ 0 to 10%;
   $K_2O$ 0 to 10 %;
   $MgO$ 0 to 10 %;
   $CaO$ 0 to 10 %;
   $SrO$ 0 to 10 %; and
   $BaO$ 0 to 10 %;

ii) heating the batch to form a glass melt, iii) conditioning the glass melt, and iv) cooling the glass melt to provide the glass element, wherein at least one, and preferably all, of the following conditions is or are fulfilled during the steps ii) and/or iii):

a) the glass melt is heated and/or warmed at least in part by an electric resistance heater by subjecting electrodes to a heating current, wherein, as heating current, an alternating current with a frequency of between 1 kHz and 200 kHz is used;

b) the contact surface with which the glass melt is in contact comprises up to 30% or more contact material in the form of melt-cast zirconium oxide material with a proportion of over 70 wt % $ZrO_2$, preferably melt-cast zirconium oxide material with a proportion of over 85 wt % $ZrO_2$; and c) between 1% and 50% of the volumetric flow is withdrawn from the bottom material of the glass melt in a bottom region of the glass melt.

The present disclosure achieves the aforementioned objects by a glass melting apparatus for carrying out a method, comprising a heating device for heating a batch to form a glass melt,
  a conditioning device for conditioning the glass melt, and
  a bottom withdrawal device for withdrawing bottom material from the glass melt,
  wherein the heating device and/or the conditioning device comprise or comprises a heating device with at least two electrodes for resistance heating; and wherein
  A) the heating device is designed or controlled in such a way that the at least two electrodes are subjected to a heating current in the form of an alternating current with a frequency of between 1 kHz and 200 kHz; and/or
  B) the contact surface with which the glass melt is in contact is designed in such a way that it comprises up to 30% or more contact material in the form of melt-cast zirconium oxide material with a proportion of over 70 wt % ZrO2, preferably melt-cast zirconium oxide material with a proportion of over 85 wt % ZrO2; and/or
  C) the bottom withdrawal device is designed in such a way so as to withdraw between 1% and 50% of the volumetric flow from the bottom material of the glass melt in a bottom region of the heating device and/or conditioning device.

The present disclosure achieves the aforementioned objects also by a method for operating a glass melting apparatus in accordance with claim 16, wherein at least one, and preferably all, of the following steps is or are carried out:

I) operating the heating device by subjecting the electrodes to a heating current, wherein, as heating current, an alternating current with a frequency of between 1 kHz and 200 kHz is used,
  II) bringing the glass melt into contact with a contact surface with which the glass melt is in contact, which surface comprises up to 30% or more melt-cast zirconium oxide material with a proportion of over 70 wt % ZrO2, preferably melt-cast zirconium oxide material with a proportion of over 85 wt % ZrO2; and
  III) operating the bottom withdrawal device in such a way that between 1% and 50% of the volumetric flow is withdrawn from the bottom material of the glass melt in a bottom region.

Beyond this, the present disclosure also achieves the aforementioned objects by a glass element, preferably a glass element made of borosilicate glass, preferably in the form of a borosilicate glass plate.

The term zirconium oxide is herein understood to mean ZrO2.

Unless otherwise defined, % herein is equivalent to wt %.

One of the advantages thereby achieved is that, in this way, inclusions, that is, metallic and nonmetallic inclusions, as well as bubbles can be substantially reduced. Preferably, when the steps ii) to iii) are carried out and when all conditions a) to c) or A) to C) are fulfilled or the steps I) to III) are carried out, it is possible to substantially lower both the number of metallic inclusions as well as the number of nonmetallic inclusions, in particular of refractory material and of recrystallization products of corrosion products dissolved in the glass. It has thereby been recognized in accordance with the disclosure that, preferably when the condition a) or A) is fulfilled or when step I) is carried out, the number of metallic inclusions is reduced. If the frequency range in accordance with the disclosure is not attained, it has been recognized that, surprisingly, the number of metallic inclusions has increased, whereas an increase in the frequency beyond the above-mentioned frequency range can be implemented only extremely tediously and thus only in a cost-intensive manner. If condition b) or B) is fulfilled or step II) is carried out, it has been recognized that, in accordance with the disclosure, this makes possible a reduction of nonmetallic inclusions of refractory material. If condition c) or C) is fulfilled or step III) is carried out, it has been recognized that, in accordance with the disclosure, this leads to the reduction of inclusions of recrystallization products of corrosion products dissolved in the glass.

Preferred embodiments are those in which condition(s) or step(s) a, A or I; b, B or II; c, C or III; a, A or I and b, B or II; a, A or I and c, C or III; b, B or II and c, C or III; or a, A or I and b, B or II and c, C or III are fulfilled or are carried out.

In accordance with a preferred embodiment, the glass element is a glass plate; a pharmaceutical primary packaging made of glass, preferably a glass vial, a glass syringe, a glass ampoule and/or a glass carpule, or a glass tube, preferably produced from borosilicate glass.

The term "bottom material" in regard to the term "glass melt" is understood to mean that material region of the glass melt that can be withdrawn through openings in the bottom, such as, for example, through an opening in a tank of the heating device and/or of the conditioning device, preferably of the conditioning device. Withdrawal of a certain % of the volumetric flow from the bottom material of the glass melt in a bottom region of the glass melt means here, in general, that a certain vol. % proportion of the glass melt in the bottom region is withdrawn per unit time. Only the supernatant portion of the glass melt serves to form the glass element, preferably in the form of a glass plate. The withdrawal out of the opening/openings in the bottom and the withdrawal of the supernatant portion of the glass melt afford in total 100% of the volumetric flow. If, for example, within a time interval, 25 liters are withdrawn from the bottom material of the glass melt in a bottom region of the glass melt and if, within the same time interval, 75 liters of the glass melt are withdrawn for formation of the glass element, preferably the glass plate, then this corresponds to a withdrawal of 25% of the volumetric flow from the bottom material of the glass melt in a bottom region of the glass melt.

The term "contact surface" in regard to the term "glass melt" is understood to mean the surface that is in contact with or comes into contact with the molten glass. This comprises, for example, the inner wall of the melting tank, also referred to as the working tank, in the case of the usual degree of filling, the stirrer, the electrode holders and the electrodes, inlets and outlets of the respective tanks (tank sections), channels inside of the melting tank, and the like. Not included in the contact surface are herein, in particular, surfaces of a device for feeding the batch into the melting tank and contact surfaces after the direct outlets from the melting tank, such as, for example, the float bath and/or the cooling channel.

The term "glass element" is understood to mean any shaped three-dimensional object that is produced at least in part, preferably predominantly, preferably completely from glass, more preferably borosilicate glass, and that can be designed preferably as a glass plate, as a pharmaceutical primary packaging made of glass, preferably as a glass vial, as a glass syringe, as a glass ampoule, and/or as a glass carpule; or as a glass tube.

The term "glass plate" is understood to mean a three-dimensional object that, in the simplest case, for example, is designed essentially as a cuboid with a thickness, a length, and a width. The smallest dimension is the thickness and the two largest dimensions represent a surface with a length and a width. The plane of view is along a normal line to the surface.

The thickness, length and width can be chosen freely. Preferably, the thickness is between 0.01 cm and 10 cm, more preferably between 0.1 cm and 5 cm, more preferably between 0.15 cm and 2.5 cm, most preferably between 0.2 and 0.4 cm. Preferably, the length and width are each between 1 cm and 500 cm, more preferably between 3 cm and 400 cm, more preferably between 5 and 100 cm, more preferably between 20 and 70 cm, most preferably 40 cm to 60 cm. The advantage thereof is the provision of a thin transparent glass plate, such as, for example, as a transparent cover or the like.

The term "glass tube" is understood to mean a three-dimensional object made of glass that, for example, in the simplest case, is designed essentially as an oblong hollow body with an outer diameter, a length, and a wall thickness. The smallest dimension is, for example, the wall thickness and the two larger dimensions are the outer diameter and the length. The plane of view is along a normal line to the outer surface of the tube.

The outer diameter, length, and wall thickness can be chosen freely. Preferably, the length of the glass tube is 2 cm or more, preferably 10 cm or more, more preferably 20 cm or more, more preferably 30 cm or more, more preferably 40 cm or more, more preferably 50 cm or more, more preferably 110 cm or more, and/or 500 cm or less, preferably 400 cm or less, more preferably 300 cm or less, more preferably 200 cm or less, more preferably 100 cm or less, more preferably 50 cm or less. Preferably, the outer diameter is 3 mm or more, preferably 4 mm or more, more preferably 5 mm or more, more preferably 6 mm or more, more preferably 7 mm or more, more preferably 8 mm or more, more preferably 9 mm or more, more preferably 10 mm or more, more preferably 15 mm or more, more preferably 20 mm or more, and/or 20 cm or less, preferably 15 cm or less, more preferably 10 cm or less, more preferably 5 cm or less, more preferably 4 cm or less, more preferably 3 cm or less, more preferably 2 cm or less. Preferably, the wall thickness is 0.1 mm, preferably 0.5 mm, more preferably 0.8 mm, more preferably 1.0 mm, more preferably 1.5 mm, more preferably 2.0 mm, more preferably 3.0 mm, and/or 10.0 mm or less, preferably 5.0 mm or less, more preferably 5.0 mm or less, more preferably 4.0 mm or less, more preferably 3.0 mm or less, more preferably 2.0 mm or less, more preferably 1.0 mm or less.

The transmission of the glass element is not limited in any special way. Preferably, the transmission of the glass element is normalized to a glass element, preferably to a glass plate or glass tube, with a thickness or wall thickness of 6.5 mm at a wavelength of 400 nm to 800 nm at 70% or more, more preferably 80% or more, more preferably 90% or more, most preferably 95% or more. The transmission is usually measured using a UV-VIS spectrometer, such as, for example, the spectral photometer Specord 250 Plus (company: Analytik Jena). The transmission of the sample is measured in the wavelength range of 250 to 1050 nm; the evaluation of the measurement is usually provided in accordance with DIN*EN 410:2011-04 (Glass in construction—

* DIN=German Industrial Standard

Determination of the luminous and solar characteristics of glazing: German Version EN 410:2011).

The determination of the number of inclusions and the size of the inclusions in accordance with embodiments of the disclosure was carried out by means of the method described below:

In a glass element to be investigated—in this case, a glass plate—visible light is coupled-in in a dark room perpendicular to the extension of the thickness of the glass plate, preferably at a straight cut edge, and parallel to the surface that is formed by the two largest dimensions (length and width). The inclusions are identified due to the reflection of the light at the inclusions in the glass plate. For differentiating between dust and inclusions in the glass plate of small particles roughly in the size range <20 μm, it is possible to use a handheld microscope, such as, for example, a "Wide Stand Microscope" handheld microscope of the PEAK company. The particles thereby identified optically are visibly marked. The glass plate marked in this way is viewed along the normal line to the surface under a light microscope, such as, for example, the Axio Imager M2m of the Zeiss company, using the LD EC Epiplan 50×/0.55 HD DIC objective and PI 10×/2 eyepiece, whereby the inclusions are classified and the size of the inclusions is measured. The size of the inclusions and particles herein relates to the longest visible dimension in the plane of view. In this kind of measurement, it is explicitly taken into account that, in the measurement, three-dimensionally formed inclusions can extend in terms of their maximum length extension also in the direction of the optical axis of the microscope, that is, along the normal line of the plane of view, and, in this case, a measured value of the inclusion is then obtained that is smaller than the actual value of the present length extension of the inclusion, such as, for example, of the crystal or crystallite. The minimum size of the inclusion that is or can be measured using the Axio Imager M2m of the company Zeiss company is approximately 2 μm. Smaller inclusions below a size of 2 μm are thus correspondingly not taken into consideration in counting the inclusions.

Even though it is not described in detail, a person skilled in the art has no problem in applying the above-described method to a glass element, such as, for example, a glass tube.

Smaller inclusions below a size of 2 μm all the way down to a size of and including 50 nm can be measured, for example, by means of the x-ray microscope "Xradia 800 Ultra" of the Zeiss company. Yet smaller inclusions with a size of less than 50 nm are correspondingly not counted or taken into consideration in the sense of the disclosure.

If a glass element weighs less than one kilogram, then the inclusions are calculated in a proportional manner. If the glass element weighs more than one kilogram, then the number of inclusions is correspondingly multiplied. The weight of the glass element is not particularly limited. The glass element preferably weighs 5 g to 400 kg, more preferably 0.01 kg to 350 kg, more preferably 0.1 kg to 20 kg, more preferably 0.2 kg to 18 kg, more preferably 0.5 kg to 15 kg, most preferably 1.0 kg to 10 kg.

Insofar as not stated otherwise, all % values are to be understood to mean weight percents, abbreviated as wt %.

The term "inclusion" is to be understood herein in the broadest sense and comprises, in particular, inclusions in the form of metallic and nonmetallic inclusions, also referred to as particles, and in the form of gas(es), such as, for example, air, as well as bubbles.

The term "metallic inclusion" is herein to be understood in the broadest sense. Metallic inclusions are here, in particular, inclusions of particles comprising one metal or a plurality of metals, predominantly present in elemental form. The metal/metals of the metallic inclusions has/have accordingly an oxidation state equal to 0. Metallic inclusions comprise, in particular, precious metals and refractory metals.

The term "nonmetallic inclusion" is to be understood in the broadest sense. Nonmetallic inclusions are herein inclusions comprising cations (oxidation state >0) and anions (oxidation state <0), also referred to as salts. In particular, nonmetallic inclusions comprise particles in the form of crystals made up of glass constituents and one salt or a plurality of salts of refractory metals and precious metals, in particular crystals made up of glass constituents and one silicate or oxide or a plurality of silicates or oxides of refractory metals and precious metals.

Inclusions are counted herein as metallic inclusions when they are comprised essentially of elemental metal, that is, of approximately 100% elemental metal (oxidation state equal to 0); otherwise, the inclusions are counted as nonmetallic inclusions. A distinction between metallic and nonmetallic can be made in an optical way as described above, for example.

Refractory metals are, for example, the metals titanium, zirconium, hafnium, vanadium, niobium, tantalum, chromium, molybdenum, and tungsten.

Precious metals comprise herein semi-precious metals and are, for example, ruthenium, rhodium, palladium, osmium, iridium, platinum, silver, gold, copper, technetium, rhenium, antimony, bismuth, and polonium.

Further examples of metals that can be contained in the inclusions are magnesium, calcium, aluminum, silicon, tin (metallic inclusions), and salts thereof (nonmetallic inclusions).

The term "bubbles" is to be understood in the broadest sense. Bubbles are formed by gas inclusions in the glass, where the gas can be gaseous at room temperature (20° C.) and can also condense after cooling and can form a bubble with negative pressure.

Gases that form inclusions comprise, for example, oxygen, nitrogen, nitrogen oxides, carbon dioxide, sulfur dioxide, or the like.

Insofar as not otherwise defined, all preferred parameters and embodiments of the glass element apply likewise to the two methods as well as to the glass melting apparatus and conversely.

Further features and advantages of the disclosure and further embodiments of the disclosure are described below or thereby become obvious.

In accordance with a preferred enhancement, the glass element has, per kg of glass, 50 inclusions or fewer with a size of 500 nm or more and 10 μm or less, preferably with a size of 50 nm or more and 10 μm or less, more preferably of 10 μm or less. The advantage thereof is that a higher quality of the glass, preferably for high-energy laser applications, is provided.

In accordance with a preferred embodiment, the glass element has, per kg of glass, 2000 inclusions or fewer, preferably 1000 inclusions or fewer, more preferably 500 inclusions or fewer, more preferably 250 inclusions or fewer, more preferably 100 inclusions or fewer, more preferably 50 inclusions or fewer, having a size of 20 μm or less, preferably 30 μm or less, more preferably 40 μm or less, most preferably 50 μm or less, and a size of 2 μm or more, preferably 50 nm or more. The advantage thereof is that a higher quality of the glass, preferably for high-energy laser applications, is provided. If the number of inclusions remains the same, but they vary in a greater size range, high-energy laser applications are less affected in a detrimental manner.

The following is hereby to be taken note of:

If, for example, the number of inclusions per kg of glass is limited to 50 inclusions or fewer with a size of 10 μm or less, then a glass element in accordance with an embodiment of the present disclosure may have, per kg of glass, 50 inclusions with a size of 5 μm and 50 inclusions with a size of 40 μm. If, however, the number of inclusions per kg of glass is limited to 50 inclusions or fewer with a size of 50 μm or less, then a glass element that, for example, has, per kg of glass, 50 inclusions with a size of 5 μm and 50 inclusions with a size of 40 μm would not fulfill this condition, but a glass element that, for example, has 10 inclusions with a size of 5 μm, 20 inclusions with a size of 25 μm, and 15 inclusions with a size of 45 μm would do so.

The glass element can have any number of further larger inclusions. Large inclusions can be detected easily by means of conventional measurement technology, such as, for example, directly after production of the glass element and/or prior to further processing, and the glass element can be sorted out entirely or in part. The embodiments of the disclosure described herein can also markedly reduce larger inclusions. Therefore, the glass element preferably has no inclusions with a size of more than 50 μm, more preferably more than 40 μm, more preferably more than 30 μm, more preferably more than 20 μm, most preferably more than 10 μm.

In accordance with a preferred embodiment, the glass element has, per kg of glass, 50 inclusions or fewer, preferably 40 inclusions or fewer, preferably 30 inclusions or fewer, more preferably 20 inclusions or fewer, most preferably 10 inclusions or fewer, wherein they can have a size of 10 μm or less, preferably 20 μm or less, preferably 30 μm or less, more preferably 40 μm or less, most preferably 50 μm or less. The advantage thereof is that the quality of the glass element, preferably for high-energy laser applications, is increased. The fewer inclusions are present per kg of glass, the less are high-energy laser applications adversely affected. The quality of the glass element is improved.

Depending on the variation of the parameters, that is, the frequency of the alternating current, the percentage withdrawal of the volumetric flow, and the proportion of zirconium oxide in the contact surface, it is possible to influence both the number of the inclusions and the size thereof. Even if only one condition a) or A), b) or B), and c) or C) is fulfilled or when only one step I), II), or III) is carried out, at least one of the parameters specifying the size of the inclusions and/or the number of the inclusions per kg of glass is reduced.

In accordance with a preferred embodiment, the inclusions comprise metallic inclusions, wherein the glass element has, per kg of glass, 40 metallic inclusions or fewer, preferably 30 metallic inclusions or fewer, more preferably 20 metallic inclusions or fewer, more preferably 10 metallic inclusions or fewer, most preferably 5 metallic inclusions or fewer, with a size of 5 μm or less, preferably 10 μm or less, more preferably 20 μm or less, more preferably 30 μm or less, more preferably 40 μm or less, most preferably 50 μm or less. Accordingly, the glass element has in total few inclusions due to metallic particles and the quality of the glass element is thereby further improved. Frequently occurring metallic inclusions comprise, in particular, metals such as tungsten, zirconium, platinum, rhodium, iridium, molybdenum, tin, and copper, because they come into contact with the glass during the production of glass elements.

In accordance with a preferred embodiment, the inclusions comprise nonmetallic inclusions, wherein the glass element has, per kg of glass, 25 nonmetallic inclusions or fewer, preferably 15 nonmetallic inclusions or fewer, more preferably 8 nonmetallic inclusions or fewer, more preferably 1 nonmetallic inclusion or fewer, more preferably 0.1 nonmetallic inclusion or fewer, more preferably 0.05 non-metallic inclusion or fewer, most preferably 0.00 nonmetallic inclusions, with a size of 2 μm or more and 10 μm or less, preferably 2 μm or more and 20 μm or less, more preferably 2 μm or more and 30 pm or less, more preferably 2 μm or more and 40 μm or less, most preferably 2 μm or more and 50 μm or less. This reduces both the number and the size of the nonmetallic inclusions, thereby, in turn, increasing the quality of the glass element. Frequently occurring nonmetallic inclusions comprise, in particular, crystals made up of glass constituents and/or one silicate and/or oxide or a plurality of silicates and/or oxides of refractory metals and/or precious metals. The crystals crystallize, for example, out of the glass melt, whereas silicates and/or oxides of refractory metals and/or precious metals are formed from the contact material that is contact with the glass melt.

In accordance with a preferred embodiment, the inclusions comprise bubbles, wherein the glass element has, per kg of glass, 25 bubbles or fewer, preferably 15 bubbles or fewer, more preferably 8 bubbles or fewer, more preferably 1 bubble or fewer, more preferably 0.1 bubble or fewer, more preferably 0.05 bubble or fewer, most preferably 0.00 bubbles, with a size of 10 μm or less, preferably 20 μm or less, more preferably 30 μm or less, more preferably 40 μm or less, most preferably 50 μm or less, and/or 2 μm or more, preferably 50 nm or more. Accordingly, the quality of the glass element is increased overall also for inclusions in the form of bubbles.

In accordance with a preferred embodiment, the composition of the glass element comprises, in wt %:

SiO2 60 to 90%, more preferably 76% to 90%;
B2O3 0 to 20%;
Al2O3 0 to 20%;
Li2O 0 to 10%;
Na2O 0 to 10%;
K2O 0 to 10 %;
MgO 0 to 10 %;
CaO 0 to 10%;
SrO 0 to 10 %; and
BaO 0 to 10%.

In a further preferred embodiment, the glass element has the following composition, in wt %:

SiO2 more than 76%;
B2O3 0 to 15%;
Al2O3 0 to 5 %;
Li2O 0 to 4 %;
Na2O 0 to 4%;
K2O 0 to 4 %;
MgO 0 to 4 %;
CaO 0 to 4 %;
SrO 0 to 4 %; and
BaO 0 to 4 %; and
unavoidable impurities, that is, under 0.01%.

In a further preferred embodiment, the glass element has the following composition, in wt %:

SiO2 76 % to 85 %;
B2O3 0 to 15%;
Al2O3 0 to 5%;
Li2O 0 to 4 %;
Na2O 0 to 4%;
K2O 0 to 4 %;
MgO 0 to 4 %;
CaO 0 to 4 %;

SrO 0 to 4 %; and
BaO 0 to 4 % and
unavoidable impurities, that is, under 0.01%.

Preferably, the glass element has iron, arsenic, and/or antimony oxide in a weight proportion of under 0.05 wt %, more preferably under 0.01 wt %. More preferably, the glass element is free of iron, arsenic, and antimony oxide. As a result of a glass element that is free of iron, arsenic, and antimony, an environmentally friendly glass element is obtained. Iron oxide can occur as an impurity and can therefore adversely affect the color of the glass element. This can be suppressed by way of a suitable selection of the starting materials.

In accordance with a preferred embodiment, the glass element has one or a plurality of the following features:

i) the weight of the glass element is 0.01 kg to 350 kg, preferably 0.1 kg to 20 kg, more preferably 0.5 kg to 15 kg, most preferably 1.0 kg to 10 kg;

ii) the thickness of the glass element, when it is provided in the form of a glass plate, is between 0.01 cm and 10 cm, preferably between 0.1 cm and 5 cm, more preferably between 0.15 cm and 2.5 cm, most preferably between 0.2 and 0.4 cm;

iii) the length and width of the glass element, when it is provided in the form of a glass plate, is in each case between 1 cm and 500 cm, preferably between 3 cm and 400 cm, more preferably between 5 and 100 cm, more preferably between 20 and 70 cm, most preferably 40 cm to 60 cm;

iv) the transmission of the glass element, normalized to a glass element in the form of a glass plate with a thickness of 6.5 mm, at a wavelength of 400 nm to 800 nm, amounts to 70% or more, more preferably 80% or more, more preferably 90% or more, most preferably 95% or more; and v) the glass element has no inclusions with a size of more than 50 μm, preferably more than 40 μm, more preferably more than 30 μm, more preferably more than 20 μm, most preferably more than 10 μm.

More preferably, the glass element has the aforementioned features i; ii; iii; iv; v; i+ii; i+iii; i+iv; i+v; ii+iii; ii+iv; ii+v; iii+iv; iii+v; iv+v; i+ii+iii; i+ii+iv; i+ii+v; i+iii+iv; i+iii+v; i+iv+v; ii+iii+iv; ii+iii+v; ii+iv+v; iii+iv+v; i+ii+iii+iv; i+ii+iii+v; i+ii+iv+v; i+iii+iv+v; or i+ii+iii+iv+v.

In accordance with a preferred embodiment of the method, the viscosity of the glass melt is brought to, and/or the value is maintained at, at least in the steps ii) and iii), a value of between 30 Pas and 450 Pas, preferably between 33 Pas and 400 Pas, more preferably between 35 Pas and 265 Pas. In accordance with a preferred embodiment of the method, the viscosity of the glass melt, at least in steps ii), is brought to, and/or the value is maintained at, a value of between 33 Pas and 265 Pas, preferably between 35 Pas and 200 Pas. In accordance with a preferred embodiment of the method, the viscosity of the glass melt, at least in steps iii), is brought to, and/or the value is maintained at a value of between 70 Pas and 450 Pas, preferably between 100 Pas and 400 Pas. One of the advantages achieved thereby is that the method can be applied to a large number of differently produced glasses with different temperatures during production.

In accordance with a preferred embodiment, the glass element is provided in the form of a glass plate or of a glass tube. This makes possible a simple production or a flexible utility of the glass element for the most varied applications.

In accordance with a preferred embodiment, the glass element has, per kg of glass, 2000 inclusions or fewer, preferably 1000 inclusions or fewer, more preferably 500 inclusions or fewer, more preferably 250 inclusions or fewer, more preferably 100 inclusions or fewer, more preferably 50 inclusions or fewer, with a size of 50 nm or more and 500 nm or less. The advantage thereof is that a higher quality of the glass, preferably for high-energy laser applications, is provided.

In accordance with a preferred embodiment, the glass element has, per kg of glass, 2000 inclusions or fewer, preferably 1000 inclusions or fewer, more preferably 500 inclusions or fewer, more preferably 250 inclusions or fewer, more preferably 100 inclusions or fewer, more preferably 50 inclusions or fewer, with a size of 500 nm or more and 2 μm or less. The advantage thereof is an even higher quality of the glass element.

In accordance with a preferred embodiment of the method, as heating current, an alternating current with a frequency of between 1 kHz and 100 kHz, preferably between 5 kHz and 50 kHz, more preferably between 8 kHz and 15 kHz, is used. If the frequency is 1 kHz or more, preferably 5 kHz or more, more preferably 8 kHz or more, the number of inclusions, in particular of metallic inclusions, is reduced. If, however, the frequency is 200 kHz or less, preferably 100 kHz or less, more preferably 50 kHz or less, more preferably 15 kHz or less, it is simpler to implement this frequency so that unanticipated problems, such as bubble formation due to local overheating, occur less often.

In accordance with a preferred embodiment of the method, the contact surface with which the glass melt is in contact is 50% or more, more preferably 60% or more, more preferably 70% or more, more preferably 80% or more, more preferably 90% or more, more preferably 95% or more of the contact material in the form of melt-cast zirconium oxide material. Accordingly, the number of inclusions of refractory material, for example, is reduced, thereby increasing overall the quality of the glass or of the glass element.

In accordance with a preferred embodiment of the method, the contact material comprises melt-cast zirconium oxide material with a proportion of over 90 wt % ZrO2, preferably over 95 wt % ZrO2. Accordingly, the number of the inclusions of refractory material is reduced still further and the quality of the glass element is increased still further.

In accordance with a preferred embodiment of the method between 5% and 40%, preferably between 20% and 40%, more preferably between 25% and 35%, of the volumetric flow is withdrawn from the bottom material of the glass melt in a bottom region. The advantage thereof is that the number of the inclusions of corrosion products, that is, of nonmetallic inclusions, is reduced and the quality of the glass is accordingly increased.

In a preferred embodiment, in the method for producing a glass element in the form of a glass plate, preferably of a borosilicate glass plate, the following steps S1 to S4—preferably first S1, then S2, then S3, and lastly S4—are carried out.

In a first step S1, a batch is provided in accordance with an embodiment of the present disclosure. In a further step S2, the batch is heated to form a glass melt. In a further step S3, there occurs a conditioning of the glass melt and, in a further step S4, there occurs a cooling of the glass melt to provide the glass element.

While steps S2—heating—and S3—conditioning—are carried out, at least one and preferably all of the following conditions is or are fulfilled:

a) the glass melt is heated and/or warmed at least in part with an electric resistance heater by subjecting electrodes to a heating current, wherein, as heating current, an alternating current with a frequency of between 1 kHz and 200 kHz is used;

b) the contact surface with which the glass melt is in contact comprises up to 30% or more contact material in the form of melt-cast zirconium oxide material with a proportion of over 70 wt % ZrO2; and c) between 1 vol. % and 50 vol. % is withdrawn from the bottom material of the glass melt in a bottom region of the glass melt.

It is understood that the aforementioned as well as the following explained features can be used not only in the respectively given combination, but also in other combinations or alone without leaving the scope of the present disclosure.

Preferred designs and embodiments of the disclosure are illustrated in the drawings and are described in detail in the following description, with identical reference numbers referring to identical or similar or functionally identical components or elements.

DETAILED DESCRIPTION OF THE DISCLOSURE

Figure 1:
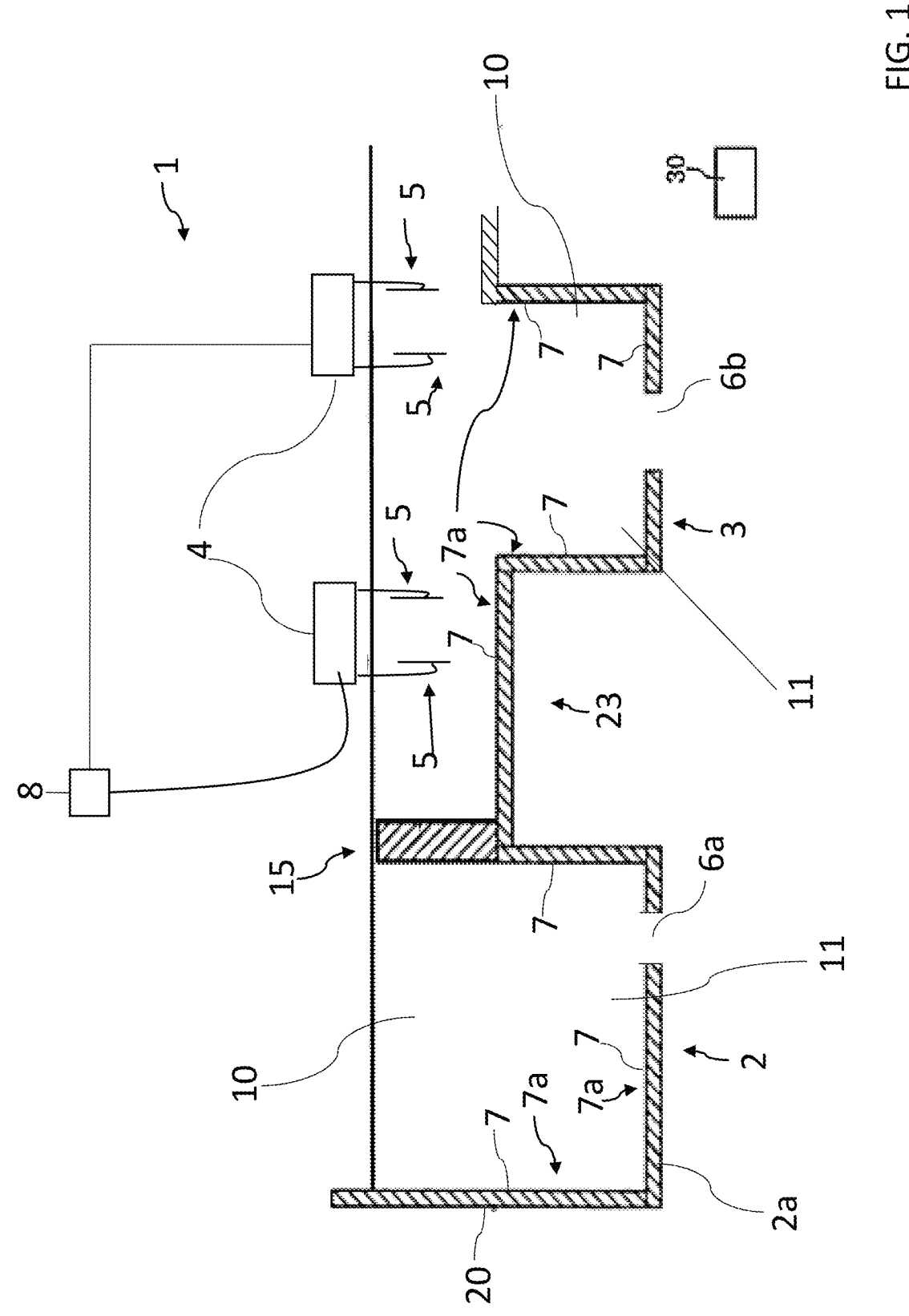
FIG. 1 is a glass melting apparatus in accordance with an embodiment of the present disclosure.

FIG. 1 shows a glass melting apparatus in accordance with an embodiment of the present disclosure.

A glass melting apparatus 1 is shown in detail in FIG. 1. The glass melting apparatus 1 comprises a heating device 2 in which the heating and melting of the starting material, that is, of the so-called batch, takes place. For this purpose, the heating device 2 has a tank 2a, which is furnished with a bottom withdrawal device 6a for withdrawing bottom material 11 of the glass melt 10.

In order to ensure an adequate homogeneity and the absence of bubbles, the melting here is followed by the refining of the glass melt 10 in a downstream situated refining device 23, which can also be employed at the same time as a transport region for transporting the glass melt 10 to a subsequent section. A key goal of the refining of the glass melt 10 is represented by the removal of physically and chemically bound gases in the glass melt 10 from the glass melt 10. After conclusion of the refining, a renewed formation of bubbles in the melt should be at least reduced or even prevented. The refining can fundamentally take place inside the same tank 2a or else in a separate tank. The refining device 23 is followed by a conditioning device 3, in which the glass melt 10 is further conditioned and/or homogenized. Situated on the bottom of the conditioning device 3 is another bottom withdrawal device 6b.

The walls 20 of the aforementioned devices 2, 23, 3 of the glass melting apparatus 1 comprise of a refractory material, such as, for example, the above-described melt-cast zirconium oxide material. In accordance with FIG. 1, the heating device 2 is separated from the refining device 23 by means of a flow-influencing element 15 that extends transverse to the flow direction over the entire width of the glass melting apparatus 1 in this region and blocks this region essentially completely, with the exception of a slight overhang to the line of position of the glass. The flow-influencing element 15 can also be arranged in an alternative or supplemental manner in the transition region between the refining device 23 and the conditioning device 3.

Furthermore, the glass melting apparatus 1 has a heating device 4 with electrodes 5 for resistance heating, which are connected to an alternating current source 8, which supplies the alternating current having a frequency of between 1 kHz and 200 kHz as heating current. In addition, the glass melt can be heated with gas burners, for example (not shown). A control device 30 controls the conditioning device 3, the heating device 2, the alternating current source 8, and, if need be, the refining device 23 as well as the bottom withdrawal devices 6a, 6b in such a way that, on the one hand, between 1% and 50% of the volumetric flow of the

| Example [Unit] | Bubbles Number/kg | Nonmetallic inclusions Number/kg | Metallic inclusions Number/kg |
|---|---|---|---|
| 1[a] | 4.7 | 33.5 | 66.8 |
| 2[b] | 0.3 | 0.2 | 53.2 |
| 3[b] | 0 | 0 | 52.4 |
| 4[b] | 0 | 0 | 8.8 |
| 5[b] | 0 | 0 | 7.7 |
| 6[b] | 0 | 0 | 6.4 |

[a]Comparative Example
[b]Example in accordance with embodiments of the disclosure The size distribution of the metallic inclusions per kg of glass of Examples 3 to 6 in the range of 0 to 50 $\mu$m is presented in the following table, in which only inclusions with a size of 2 $\mu$m or more are taken into consideration in the given size interval of 0 $\mu$m to 5 $\mu$m of the following table:

| Example [Unit] | Size in $\mu$m | | | | | |
| | 0 to 5 Number/kg | 5 to 10 Number/kg | 10 to 20 Number/kg | 20 to 30 Number/kg | 30 to 40 Number/kg | 40 to 50 Number/kg |
|---|---|---|---|---|---|---|
| 3[b] | 10.5 | 10.5 | 10.5 | 7.0 | 3.5 | 3.5 |
| 4[b] | 6.9 | 1.9 | 0 | 0 | 0 | 0 |
| 5[b] | 7.0 | 0.7 | 0 | 0 | 0 | 0 |
| 6[b] | 5.1 | 1.3 | 0 | 0 | 0 | 0 |

[b]Example in accordance with embodiments of the disclosure glass melt 10, such as, for example, 25%, of the bottom material of the glass melt is withdrawn and, if need be, can be fed back to the heating device 2 and in such a way that, on the other hand, a resistance heating of the glass melt 10 occurs at least in the conditioning device 3. Furthermore, the contact surfaces 7 that are in contact with the glass melt 10 comprise contact material 7a in the form of melt-cast zirconium oxide material with a proportion of over 70 wt % $ZrO_2$, preferably melt-cast zirconium oxide material with a proportion of over 85 wt % $ZrO_2$.

Figure 2:
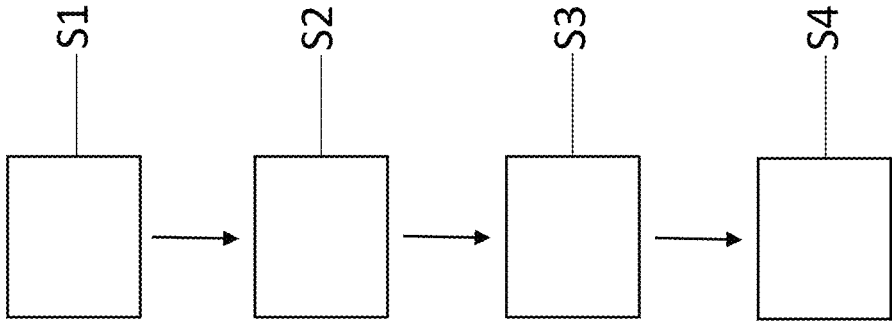
FIG. 2 is a method for producing a glass element in accordance with an embodiment of the present disclosure.

FIG. 2 shows steps of a method for producing a glass element in accordance with an embodiment of the present disclosure.

The method comprises the following steps:

In a first step S1, a batch is provided in accordance with an embodiment of the present disclosure. In a further step S2, the batch is heated to form a glass melt. In a further step S3, the glass melt is conditioned and, in a further step S4, he glass melt is cooled to provide the glass element.

In a preferred embodiment in a method for producing a glass element, preferably in the form of a glass plate, preferably of a borosilicate glass plate, the following steps S1 to S4—preferably first S1, then S2, then S3, and lastly S4—are carried out.

EXAMPLES

Shown in the following table is the total number of inclusions of a comparative example and of examples in accordance with embodiments of the disclosure, divided into various categories, namely, bubbles, nonmetallic inclusions, and metallic inclusions:

In Comparative Example 1 and Example 2, the size distribution of the inclusions was not determined exactly. In Examples 2 and 3, although the total number of inclusions was just over 50 (for example, Example 2: 0.3+0.2+53.2=53.7 per kg) per kg of glass, the size of some inclusions was over 50 $\mu$m, so that the number of inclusions with a size of 50 $\mu$m or less and thus also the number of inclusions with a size of 10 $\mu$m or less was under 50 inclusions per kg of glass (see second table; Example 3: 10.5+10.5+10.5+7.0+3.5+3.5=45.5 per kg). Besides the inclusions given in the second table, inclusions with a size over 100 $\mu$m were additionally found in Example 3. In Examples 3 to 6, the number of inclusions with a size of 50 $\mu$m or less was under 50 inclusions per kg (see second table) and, in Examples 4 to 6, even under 10 inclusions per kg. In addition, the glass plates of Examples 4 to 6 had no further inclusions with a size over 50 $\mu$m (as seen by comparison of the first and second tables).

Comparative Example 1 is an example of a glass element in the form of a glass plate, for which none of the herein described improvements were used on the glass melting apparatus. In other words, a hitherto known glass melting apparatus or a hitherto known production method was used. The total number of inclusions here was markedly over 50 and the number of inclusions in the particular category was also very high. Even through the exact size of each individual inclusion was not determined in Comparative Example 1, it may be assumed that, on account of the high number of inclusions also in the range under 50 $\mu$m, the number of the inclusions must lie markedly over 50 inclusions per kg. Proceeding therefrom, a test glass melting apparatus was successively continuously improved.

First of all, in an experiment in the glass melting apparatus, a portion of the contact surface (about 70% or more) with which the glass melt was in contact was furnished with contact material made of melt-cast zirconium oxide material with a proportion of over 70 wt % $ZrO_2$. At the same time, the glass melting apparatus was operated in such a way that between 1% and 50% of the volumetric flow was withdrawn from the bottom material of the glass melt in a bottom region of the glass melt. This led to a significant reduction of the bubbles and nonmetallic inclusions (see, for example, Example 2). The number of metallic inclusions lies in Example 2 at over 50 (number=53.2), of which, as already described above, although a large part of the inclusions had a size of 50 μm or less, some inclusions also had a size over 50 μm. Accordingly, a glass plate produced in such a way has, per kg of glass, 50 inclusions or fewer with a size of 10 μm or less. Furnishing a smaller portion of the contact surface with the special contact material (30% of contact surface or more) led to a reduction of the bubbles and nonmetallic inclusions. Zero bubbles and nonmetallic inclusions per kg having a size of 50 μm or less were found for glass plates that were produced by use of a glass melting apparatus in which a large part of the contact surface (90% or more or even 95% or more) with which the glass melt was in contact was melt-cast zirconium oxide material with a high proportion (85 wt % or more or even 95 wt % or more) of $ZrO_2$, and, in addition, a large proportion (between 25 vol. % and 35 vol. %) was withdrawn from the bottom material of the glass melt in a bottom region of the glass melt (see Examples 3 to 6).

The electric resistance heating was also optimized. To this end, for test purposes, a new electric resistance heater in accordance with an embodiment of the present disclosure was installed in the glass melting apparatus. In Comparative Example 1, a conventional resistance heater was used and a large number of metallic inclusions was determined in the glass plate produced thereby. In Examples 2 to 6, the glass melt was heated and/or warmed at least in part by means of an electric resistance heater by subjecting electrodes to a heating current, wherein, as heating current, an alternating current having a frequency of between 1 kHz and 200 kHz was used, whereby the number of metallic inclusions could be reduced. The number of metallic inclusions could be further markedly reduced by adjusting the frequency between 1 kHz and 100 kHz until, finally, especially few metallic inclusions were found at a frequency of between 8 kHz and 15 kHz (see Examples 4 to 6).

It is additionally evident from the examples that the best result is achieved when all three improvement steps described herein are employed.

In summary, at least one of the embodiments of the disclosure has at least one of the following advantages:

reduction of inclusions, preferably of inclusions of metallic particles, with a size of 50 μm or less;
increase of the flexibility of the glass in regard to various applications,
higher quality of the glass;
fewer rejects; and
reduced number of bulk defects or lower bulk defect densities.

The glass element produced by means of embodiments of the disclosure can preferably be employed or used for the following applications:

laser applications with high energy density;
large-format, homogeneous and/or low-defect photomasks for lithographic applications;
nanoimprint lithography, imprint molds for imprinting of precision lenses or nanostructures down to the nm range, such as, for example, hard-drive magnetic layers or the like;

substrates for flat metal lens designs and optics;
superglass wafers; and
precision windows in displays, preferably for OLEDs.

Although the present disclosure was described on the basis of preferred exemplary embodiments, it is not restricted to these, but can be modified in diverse ways.

What is claimed is:

1. A glass element made of borosilicate glass,
wherein the glass element has, per kg of glass, 50 inclusions or fewer having a size from 2 μm to 10 μm,
wherein the inclusions comprise gaseous inclusions, solid metallic inclusions, and solid nonmetallic inclusions,
wherein the glass element has a composition that comprises, in wt %:
$SiO_2$ 76 to 90%;
$B_2O_3$ up to 20%;
$Al_2O_3$ 0 to 20%;
$Li_2O$ 0 to 10%;
$Na_2O$ 0 to 10%;
$K_2O$ 0 to 10%;
MgO 0 to 10%;
CaO 0 to 10%;
SrO 0 to 10%; and
BaO 0 to 10%.

2. The glass element according to claim 1, wherein the glass element has, per kg of glass, 2000 inclusions or fewer having a size of 10 μm or less.

3. The glass element according to claim 1, wherein the glass element has, per kg of glass, 50 inclusions or fewer having a size from 50 nm to 50 μm.

4. The glass element according to claim 1, wherein the glass element has, per kg of glass, 40 inclusions or fewer.

5. The glass element according to claim 1, wherein the glass element has, per kg of glass, 40 metallic inclusions or fewer.

6. The glass element according to claim 1, wherein the glass element has, per kg of glass 25 nonmetallic inclusions or fewer.

7. The glass element according to claim 1, further comprising -bubbles, wherein the glass element has, per kg of glass, 25 bubbles or fewer having a size from 50 nm to 50 μm.

8. The glass element according to claim 1, wherein the glass element has at least one feature selected from the group consisting of:
i) a weight of the glass element is 0.01 kg to 350 kg;
ii) a glass plate form with a thickness from 0.01 cm to 10 cm;
iii) a glass plate form with a length and width that are each from 1 cm to 500 cm;
iv) a transmission of the glass element, normalized to a glass element in the form of a glass plate with a thickness of 6.5 mm at a wavelength of 400 nm to 800 nm, that is 70% or more; and
v) no inclusions having a size greater than 50 μm.

9. The glass element according to claim 1, wherein the glass element is a glass plate or a glass tube.

10. The glass element according to claim 1, wherein the glass element has, per kg of glass, 2000 inclusions or fewer having a size of 50 nm to 500 nm.

11. The glass element according to claim 1, wherein the glass element has, per kg of glass, 2000 inclusions or fewer having a size of 500 nm to 2 μm.

12. A method for producing a glass element made of borosilicate glass comprising the steps:
i) providing a batch, comprising, in wt %:
$SiO_2$ 60 to 90%;
$B_2O_3$ 0 to 20%;

17

$Al_2O_3$ 0 to 20%;
$Li_2O$ 0 to 10%;
$Na_2O$ 0 to 10%;
$K_2O$ 0 to 10%;
MgO 0 to 10%;
CaO 0 to 10%;
SrO 0 to 10%; and
BaO 0 to 10%;

ii) heating the batch to form a glass melt,
iii) conditioning the glass melt, and
iv) cooling the glass melt to provide the glass element,
wherein, during step ii) and/or iii):
a) the glass melt is heated at least in part with an electric resistance heater by subjecting electrodes to a heating current, wherein the heating current is an alternating current with a frequency from 1 kHz and 200 kHz is used;
b) a contact surface with which the glass melt is in contact comprises 30% or more contact material in the form of melt-cast zirconium oxide material with a proportion of over 70 wt % $ZrO_2$; and

c) from 1% to 50% of a volumetric flow is withdrawn from a bottom material of the glass melt in a bottom region of the glass melt,
wherein the glass element has, per kg of glass, 50 inclusions or fewer having a size from 2 μm to 10 μm,
wherein the inclusions comprise gaseous inclusions, solid metallic inclusions, and solid nonmetallic inclusions.

13. The method according to claim 12, further comprising during step ii) and/or iii), a viscosity of the glass melt is brought to and/or maintained at from 30 Pas and 450 Pas.

14. The method according to claim 12, wherein the alternating current has a frequency from 1 kHz to 100 KHz.

15. The method according to claim 12, further comprising a contact surface with which the glass melt is in contact comprises 60% or more contact material in the form of melt-cast zirconium oxide material with a proportion of 75 wt % or more $ZrO_2$.

16. The method according to claim 12, wherein 5% to 40% of a volumetric flow is withdrawn from a bottom material of the glass melt in a bottom region of the glass melt.

* * * * *